(12) United States Patent
Wollenweber et al.

(10) Patent No.: US 7,348,564 B2
(45) Date of Patent: Mar. 25, 2008

(54) MULTI MODALITY IMAGING METHODS AND APPARATUS

(75) Inventors: Scott David Wollenweber, Waukesha, WI (US); Albert H. R. Lonn, Beaconsfield (GB); Charles William Stearns, New Berlin, WI (US); Diane Marie Miesbauer, Hartland, WI (US); Kathryn Mary Littlejohn, Wales, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/301,149

(22) Filed: Dec. 12, 2005

(65) Prior Publication Data

US 2007/0131858 A1 Jun. 14, 2007

(51) Int. Cl.
*G01T 1/166* (2006.01)
(52) U.S. Cl. .............................. 250/363.04; 250/363.02
(58) Field of Classification Search ........... 250/363.04, 250/363.02, 363.01, 361 R, 336.1
See application file for complete search history.

(56) References Cited

U.S. PATENT DOCUMENTS

| | | | |
|---|---|---|---|
| 3,914,607 A | 10/1975 | Cho et al. | |
| 4,029,963 A | 6/1977 | Alvarez et al. | |
| 4,578,803 A | 3/1986 | Macovski | |
| 4,633,398 A | 12/1986 | Gullberg et al. | |
| 5,210,421 A | 5/1993 | Gullberg et al. | |
| 5,338,936 A * | 8/1994 | Gullberg et al. | 250/363.04 |
| 5,376,795 A | 12/1994 | Hasegawa et al. | |
| 5,608,221 A * | 3/1997 | Bertelsen et al. | 250/363.03 |
| 6,310,968 B1 * | 10/2001 | Hawkins et al. | 382/131 |
| 6,429,434 B1 * | 8/2002 | Watson et al. | 250/363.04 |
| 6,490,476 B1 * | 12/2002 | Townsend et al. | 600/427 |
| 6,631,284 B2 * | 10/2003 | Nutt et al. | 600/427 |
| 6,735,277 B2 * | 5/2004 | McNutt et al. | 378/65 |
| 6,841,782 B1 * | 1/2005 | Balan et al. | 250/363.02 |
| 6,850,585 B2 * | 2/2005 | Hsieh et al. | 378/4 |
| 6,856,666 B2 * | 2/2005 | Lonn et al. | 378/8 |
| 6,878,941 B2 * | 4/2005 | Balan et al. | 250/363.02 |
| 6,950,494 B2 * | 9/2005 | Vija et al. | 378/62 |
| 2004/0030246 A1 * | 2/2004 | Townsend et al. | 600/427 |
| 2004/0066909 A1 * | 4/2004 | Lonn et al. | 378/901 |
| 2004/0174960 A1 * | 9/2004 | Hsieh et al. | 378/210 |
| 2006/0237652 A1 * | 10/2006 | Kimchy et al. | 250/363.02 |

* cited by examiner

*Primary Examiner*—David Porta
*Assistant Examiner*—Mark R Gaworecki
(74) *Attorney, Agent, or Firm*—The Small Patent Law Group LLP; Dean D. Small (57) ABSTRACT

A method for correcting emission data from Positron Emission Tomography (PET) or SPECT includes generating a plurality of computed tomography (CT) image data, selecting a portion of the CT image data, processing the selected CT data to generate a plurality of attenuation correction (CTAC) factors at the appropriate energy of the emission data, weighting the CTAC factors to generate an emission attenuation correction map wherein the weights are determined based on the axial location and the slice thickness of the CT data and the axial location and the slice thickness of the PET or SPECT data, and utilizing the generated attenuation correction map to generate an attenuation corrected PET image.

19 Claims, 5 Drawing Sheets

MULTI MODALITY IMAGING METHODS AND APPARATUS

BACKGROUND OF THE INVENTION

This invention relates generally to image processing and image reconstruction based on acquired raw image data. In particular, improving the emission image quality in combined imaging systems such as CT-PET and CT-SPECT which use a CT image for multiple purposes including diagnostic review, fusion review with the PET, and calibration and correction of the PET data for effects including attenuation and scatter.

Raw image data from various diagnostic medical systems, such as Computed Tomography (CT), Positron Emission Tomography (PET) systems, and Single Photon Computed Tomography (SPECT) systems are acquired for diagnostic purposes. The CT PET and SPECT systems are configured to support numerous scanning and reconstruction modes. The associated reconstruction algorithms are complex and computationally intensive. Users of the diagnostic medical systems desire an improvement in image quality, to minimize the time required to generate images based on raw image data, and to improve the reliability of the reconstruction process. By decreasing the amount of time needed to generate the desired images from raw image data, images can be evaluated sooner and patient through-put may be improved.

Accordingly, at least one known PET-CT system and one known SPECT-CT system, utilizes data that are generated by the CT apparatus to generate an attenuation correction of the PET or SPECT scan data. Specifically, a plurality of emission attenuation correction factors are derived from CT data that is generated during a CT scan, wherein the CT system is specifically configured to generate data to be utilized for the CT attenuation correction factors. A method of converting the CT Hounsfield units into emission attenuation factors is described in U.S. Pat. No. 6,856,666. In this document, the term CTAC is used to denote the map of emission Attenuation Coefficients which are derived from the CT images.

For example, PET scan data is acquired and processed as a sequence of axial frames along the length of the patient. PET images are typically reconstructed at axial intervals corresponding to sub-multiples of the average axial detector spacing, for instance, half of the detector spacing. CT axial images from multislice detectors are typically reconstructed with axial intervals corresponding to multiples of the nominal detector interval. For example the PET slices are reconstructed at intervals of approximately 3.3 mm, corresponding to half the detector spacing, with a nominal slice thickness of approximately four millimeters. The CT axials images are reconstructed at intervals corresponding to multiples of the nominal detector interval of 0.625 mm. CT helical scans are normally reconstructed at intervals equal to the slice thickness, but on the GEHC PET-CT the interval for helical scans can be set to any value. For the purposes of PET attenuation correction, the CT interval is set equal to the PET interval. Accordingly, known CT/PET systems generate CT attenuation correction factors, by first generating a set of CT slices that approximately match the thickness of the PET slice, at axial locations matching the PET slices.

While appropriate for generating the CT attenuation correction factors utilized to generate a PET image, this relatively thick CT slice is generally not useful for medical imaging purposes. Specifically, CT images useful for medical diagnosis, are typically less than four millimeters thick to facilitate enhancing image resolution and thus medical diagnosis of the patient. Therefore, while generating a relatively thick CT slice is beneficial to generate the attenuation correction factors used to generate the PET image, the relatively thick CT slice may not have the image quality or resolution to allow an operator to perform a medical diagnosis of the patient using the generated CT image.

BRIEF DESCRIPTION OF THE INVENTION

In one aspect, a method for correcting emission data from Positron Emission Tomography (PET) or SPECT data is provided. The method includes generating a plurality of computed tomography (CT) image data, selecting a portion of the CT image data, processing the selected CT data to generate a plurality of attenuation correction (CTAC) factors at the appropriate energy of the emission data, weighting the CTAC factors to generate an emission attenuation correction map wherein the weights are determined based on the axial location and the slice thickness of the CT data and the axial location and the slice thickness of the PET data, and utilizing the generated attenuation correction map to generate an attenuation corrected PET image.

In another aspect, an imaging system is provided. The imaging system includes a CT unit having a patient bore therethrough, a PET unit having a patient bore therethrough, a control mechanism communicatively coupled to the CT and PET units to control movement of the CT and PET units, and a computer coupled to the CT and PET units. The computer is programmed to process selected portion of CT data to generate a plurality of attenuation correction (CTAC) factors, weight the CTAC factors to generate a PET attenuation correction map wherein the weights are determined based on the axial location and the slice thickness of the CT data and the axial location and the slice thickness of the PET data, and utilize the generated attenuation correction map to generate an attenuation corrected PET image.

In a further aspect, a computer program is provided. The computer program is configured to process selected portion of CT data to generate a plurality of computed tomography attenuation correction (CTAC) factors, weight the CTAC factors to generate a PET attenuation correction map wherein the weights are determined based on the axial location and the slice thickness of the CT data and the axial location and the slice thickness of the PET data, and utilize the generated attenuation correction map to generate an attenuation corrected PET image.

DETAILED DESCRIPTION OF THE INVENTION

There is herein provided a system and method for correcting Positron Emission Tomography (PET) data. The apparatus and methods are illustrated with reference to the figures wherein similar numbers indicate the same elements in all figures. Such figures are intended to be illustrative rather than limiting and are included herewith to facilitate explanation. of an exemplary embodiment of the apparatus and methods of the invention.

At least some multi-modality systems have different fields of views (FOVs) for the different modalities. For example, a CT/PET system may have a CT FOV which is smaller than a PET FOV, and under some scanning conditions, portions of a patient may extend beyond the region measured by a CT detector, which may lead to image artifacts and an incomplete representation of the imaged object. Some known methods have been published that address the artifact reduction but not the imaging of the portion of the patient that is outside the CT FOV.

In such multi-modality systems, such as, for example, an integrated PET-CT system there is an inherent registration of the PET and CT images the system acquires. Since the patient lies still on the same table during the PET and CT portions of the acquisition, the patient will be in a consistent position and orientation during the two acquisitions, greatly simplifying the process of correlating and fusing the CT and PET images. This allows the CT image to be used to provide attenuation correction information for the reconstruction of the PET image, and allows an image reader to easily correlate the anatomic information presented in the CT image and the functional information presented in the PET image. However, it is desirable to provide attenuation information for the reconstruction of the PET image of the portion of the patient that extends beyond the CT FOV. It is also desirable to provide accurate attenuation information for the PET image inside the FOV (Note that artifacts caused by truncation produce biased attenuation information).

Figure 1:
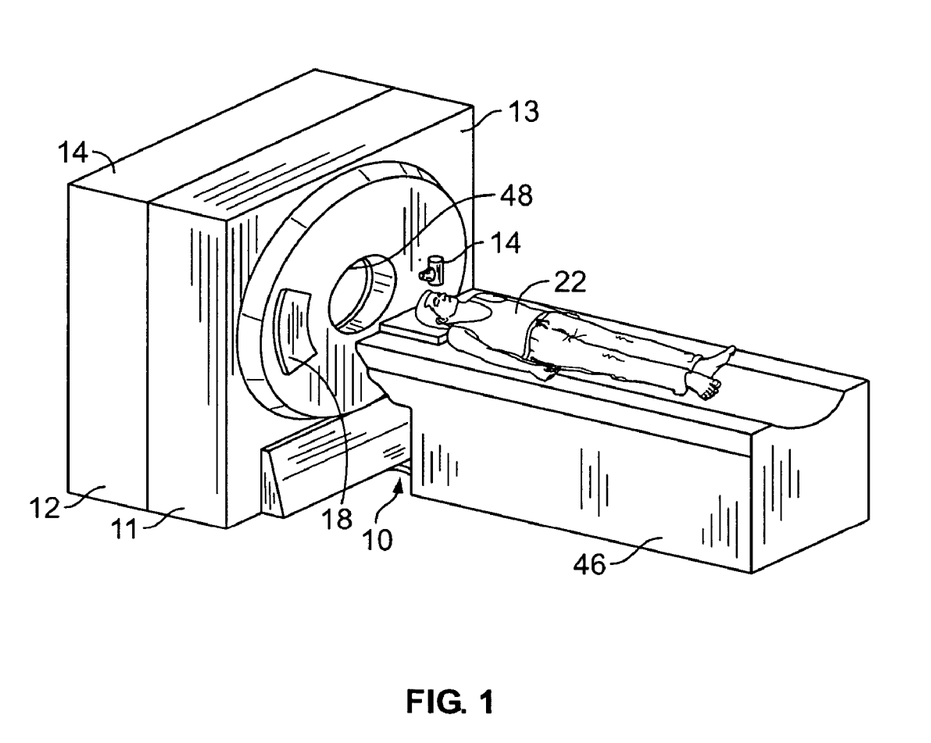
FIG. 1 is a pictorial view of a CT imaging system embodiment.
Figure 2:
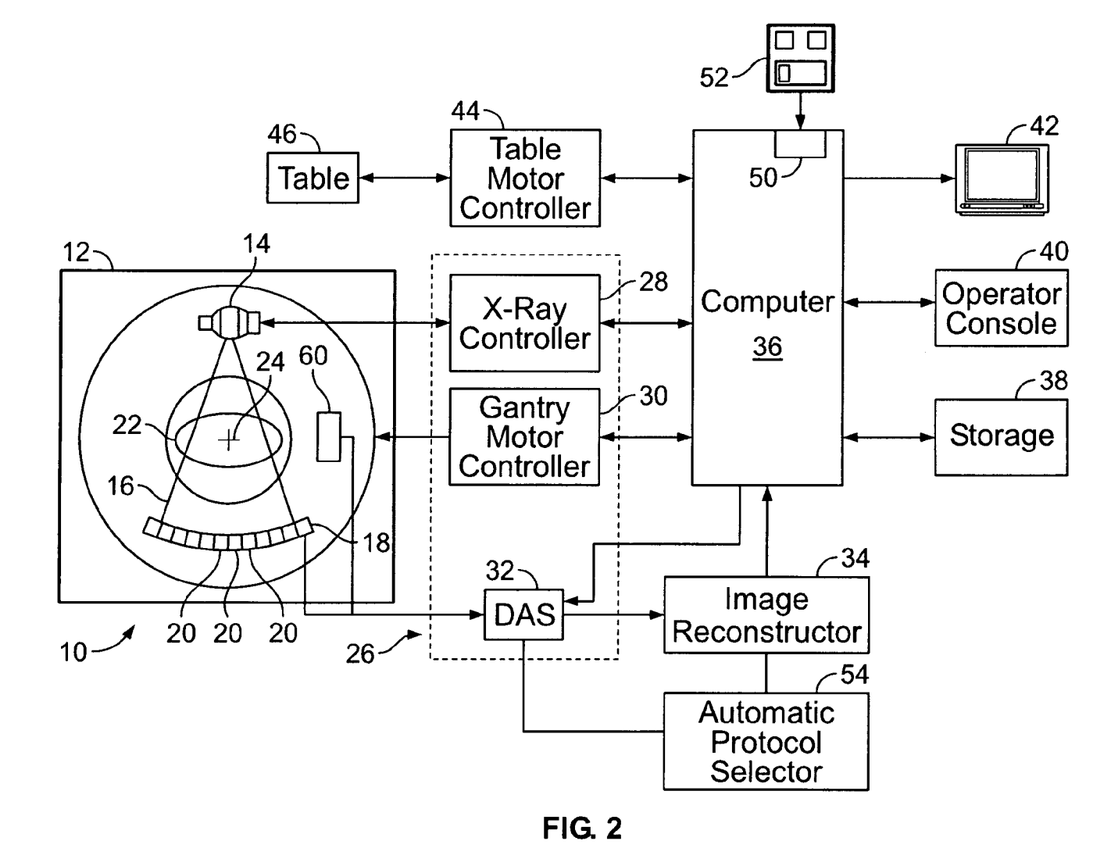
FIG. 2 is a block schematic diagram of the system illustrated in FIG. 1.

Referring to FIGS. 1 and 2, a multi-modal imaging system 10 is illustrated, and includes a first modality unit and a second modality unit. The two modality units enable system 10 to scan an object in a first modality using the first modality unit and to scan the object in a second modality using the second modality unit. System 10 allows for multiple scans in different modalities to facilitate an increased diagnostic capability over single modality systems. In one embodiment, multi-modal imaging system 10 is a Computed Tomography/Positron Emission Tomography (CT/PET) imaging system 10. Optionally, modalities other than CT and PET are employed with system 10. The first modality unit, i.e. the CT imaging system, includes a gantry 12 which has an x-ray source 14 that projects a beam of x-rays 16 toward a detector array 18 on the opposite side of gantry 12. Detector array 18 is formed by a plurality of detector rows that each include a plurality of detector elements 20 which together sense the projected x-rays that pass through an object, such as a medical patient 22. Each detector element 20 produces an electrical signal that represents the intensity of an impinging X-ray beam and hence allows estimation of the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, a multislice detector array 18 includes a plurality of parallel detector rows of detector elements 20 such that projection data corresponding to a plurality of slices can be acquired simultaneously during a scan.

Rotation of gantry 12 and the operation of x-ray source 14 are governed by a control mechanism 26 of CT/PET system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives the sampled and digitized x-ray data from DAS 32 and performs high-speed image reconstruction. The reconstructed image is applied as an input to a computer 36 which stores the image in a storage device 38. Computer 36 also receives commands and scanning parameters from an operator via console 40 that has a keyboard. An associated visual display unit 42 allows the operator to observe the reconstructed image and other data from computer.

The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves at least a portion of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

CT/PET system 10 also includes a second imaging modality that includes a PET emission detector 60 including a plurality of detector elements (not shown). The PET emission detector 60 and CT detector array 18 both detect radiation and are both referred to herein as radiation detectors. In one embodiment, CT/PET system 10 is a Discovery LS CT/PET system commercially available from General Electric Medical Systems, Waukesha Wis., and configured as herein described. In another embodiment, CT/PET system 10 is a Hawkeye CT/PET/SPECT system also commercially available from GE Healthcare Waukesha Wis., and configured as herein described. Additionally, although described in a medical setting, it is contemplated that the benefits of the invention described herein may also accrue to all multi-modality imaging systems.

The detector 18 has a plurality of rows (not shown ) each having a plurality of elements 20 which detect the X rays 16 passing through the patient 20 The intensity of the attenuated radiation beam 16 received at the detector array 18 is dependent upon the attenuation of an x-ray beam 16 by the patient 24. In the exemplary embodiment, object 24 is a patient 24. Each detector element 20 of the array 18 produces a separate electrical signal that is a measurement of the beam intensity at the detector location. The intensity measurements from all the detectors 20 are acquired separately to produce a transmission profile.

In the exemplary embodiment, the x-ray source 14 and the detector array 18 are rotated with a gantry 12 within the imaging plane and around the patient 24 to be imaged such that the angle at which the x-ray beam 16 intersects the patient 24 constantly changes. A group of x-ray attenuation measurements, i.e., projection data, from the detector array 18 at one gantry angle is referred to as a "view". A "scan" of the patient 24 comprises a set of views made at different gantry angles, or view angles, during one revolution of the x-ray source 14 and detector 18.

In an axial scan, the projection data is processed to construct an image that corresponds to a two dimensional slice taken through the patient 24. One method for reconstructing an image from a set of projection data is referred to in the art as the filtered back projection technique. This process converts the integral attenuation measurements into an image representing attenuation of the patient in each pixel. The attenuation measurements are typically converted into units of CT numbers or Hounsfield units.

To reduce the total scan time, a "helical" scan may be performed. To perform a "helical" scan, the patient 24 is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to the filtered back projection process, the data is weighted according to a helical weighing factor, which is a function of both the gantry angle and detector angle. The weighted data is then processed to generate CT numbers and to construct an image that corresponds to a two dimensional slice taken through the patient 24.

During operation of multi-slice CT/PET system 10, multiple projections are acquired simultaneously with multiple detector rows. Similar to the case of helical scan, weighting functions are applied to the projection data prior to the filtered back projection process.

Additionally, as described previously herein, system 10 is also configured to perform Positron Emission Tomography (PET). During operation, positrons, i.e. positively charged electrons or anti-electrons, are emitted by radionuclides that have been prepared using a cyclotron or other device. The radionuclides most often employed in diagnostic imaging are fluorine-18 (18F), carbon-11 (11C), nitrogen-13 (13N), and oxygen-15 (15O). Radionuclides are employed as radioactive tracers called "radiopharmaceuticals" by incorporating them into substances such as glucose or carbon dioxide.

In typical use, the radiopharmaceutical is injected into a patient, such as patient 24, and accumulates in an organ, vessel or the like, which is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism, fatty acid metabolism and protein synthesis.

After the radiopharmaceutical becomes concentrated within an organ of interest and while the radionuclides decay, the radionuclides emit positrons. The positrons travel a very short distance before they encounter an electron and, when the positron encounters an electron, the positron is annihilated and converted into two photons. This annihilation event is characterized by two features which are pertinent to imaging and particularly to medical imaging using photon emission tomography (PET). First, each annihilation photon has an energy of approximately 511 keV upon annihilation. Second, the two annihilation photons are directed in substantially opposite directions.

In PET imaging, if the general locations of annihilations can be identified in three dimensions, a three dimensional image of an organ of interest can be reconstructed for observation. To detect annihilation locations, a PET camera, such as emission detector 60, for example, is employed. An exemplary PET camera includes a plurality of detectors and a processor which, among other things, includes coincidence detection circuitry.

The coincidence circuitry (not shown) identifies essentially simultaneous pulse pairs which correspond to detectors which are essentially on opposite sides of the imaging area. Thus, a simultaneous pulse pair indicates that an annihilation event has occurred on a straight line between an associated pair of detectors. Over an acquisition period of a few minutes, millions of annihilations are recorded, and each annihilation is associated with a particular detector pair via DAS 32, for example. After an acquisition period, recorded annihilation data can be used via any of several different well-known back projection procedures to construct the three dimensional image of the organ of interest.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

As described previously herein, CT/PET system 10 is configured to utilize data that is generated operating the CT modality of system 10 to generate attenuation correction factors that are utilized during operation of the PET modality of system 10. Specifically, the emission attenuation correction factors (CTAC) are derived from CT data that is generated during a CT scan, wherein the CT system is configured to generate CT data at a spacing and technique that produces the best CT image quality and to utilize the same CT image data to generate an attenuation-corrected PET image.

More specifically, and in the exemplary embodiment, a patient 24 is scanned utilizing CT/PET imaging system 10 to generate 102 a plurality of CT images. As discussed herein, the term "image" broadly refers to both viewable images and data representing a viewable image. The generated images are then utilized to generate a plurality of CT attenuation correction factors.

Figure 3:
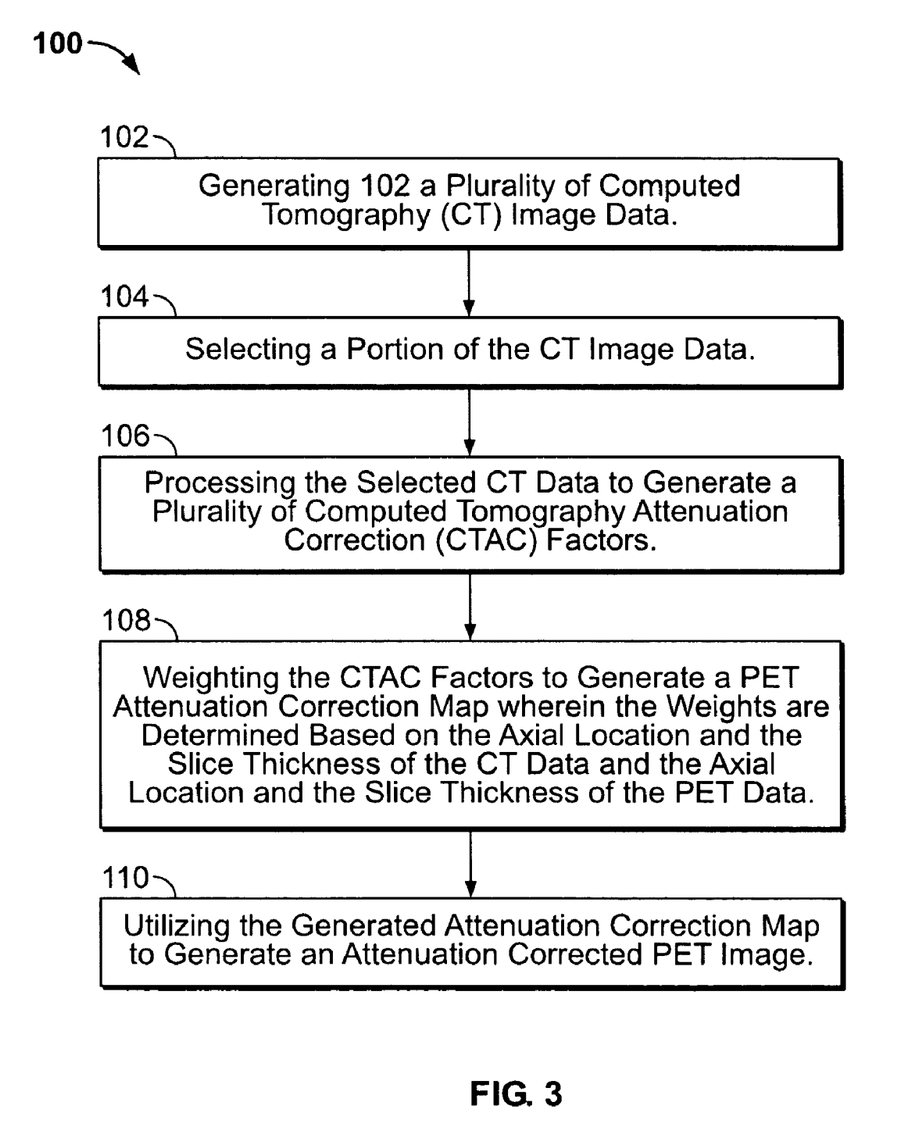
FIG. 3 is a flowchart illustrating a method for correcting Positron Emission Tomography (PET) data.

FIG. 3 is a flowchart illustrating an exemplary method 100 of correcting Positron Emission Tomography (PET) data. In the exemplary embodiment, method 100 includes generating 102 a plurality of computed tomography (CT) image data, selecting 104 a portion of the CT image data, processing 106 the selected CT data to generate a plurality of emission attenuation correction (CTAC) factors, weighting 108 the CTAC factors to generate a PET attenuation correction map wherein the weights are determined based on the axial location and the slice thickness of the CT data and the axial location and the slice thickness of the PET data, and utilizing 110 the generated attenuation correction map to generate an attenuation corrected PET image. The process 106 of converting the CT image data into emission attenuation factors (CTAC) comprises reducing the resolution of the CT image data to match the emission resolution, and converting the CT units into attenuation coefficients using a conversion based on the CT pixel value, the nominal X-ray tube voltage setting , and the attenuation coefficents of water and bone at the emission energy.

Alternatively, if all the selected CT images have the same characteristics, such as the kV, which enables the use of the same conversion factors from CT units to emission attenuation coefficients, the process 106 of converting the CT image units into attenuation may be performed after the processing 108.

Figure 4:
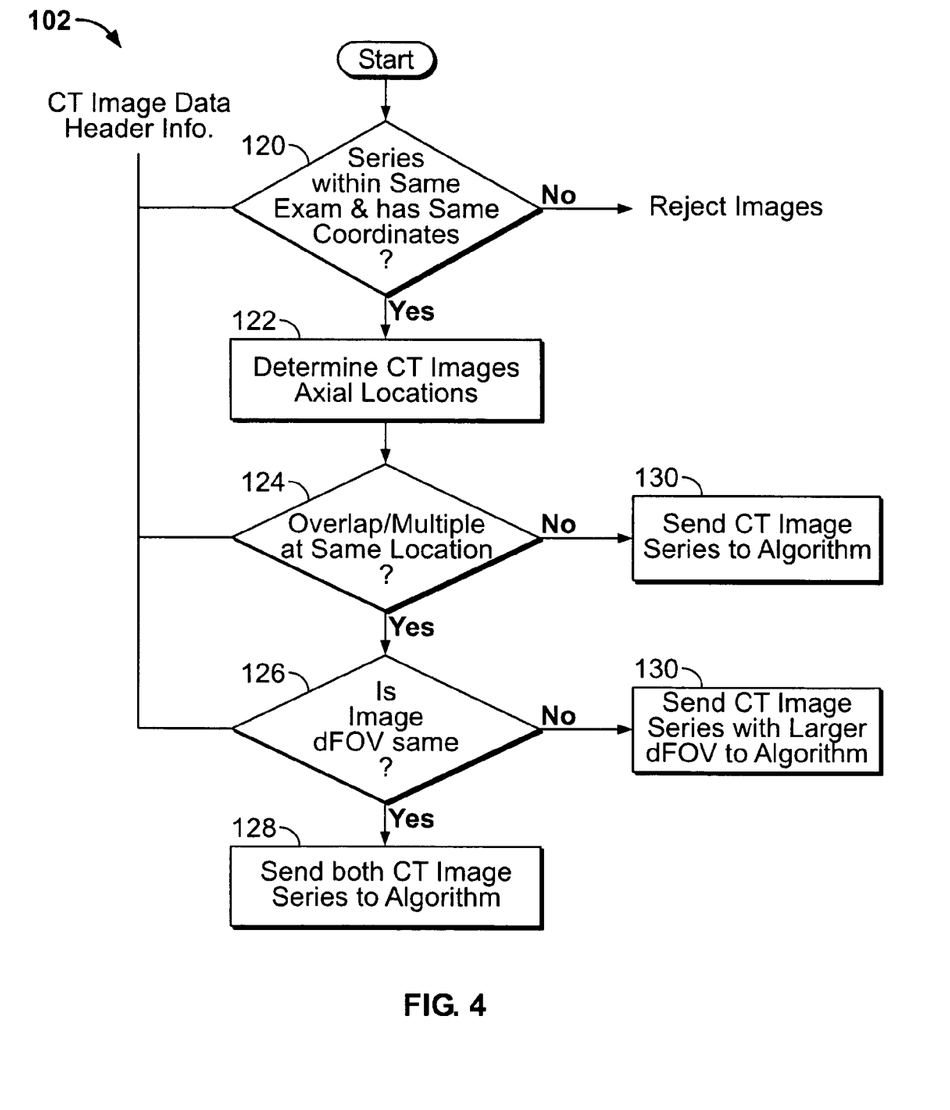
FIG. 4 is a flowchart illustration a portion of the method shown in FIG. 4.

FIG. 4 is a flowchart illustrating an exemplary method of selecting 102 CT imaging data that can be utilized to generate a plurality of attenuation correction factors (CTAC). More specifically, after a CT scan is performed, the generated CT image data is utilized by an operator to determine the location or coordinates in which a PET scan is to be performed. For example, if a CT scan is performed over the entire torso region, an operator may desire to conduct a PET scan over only a portion of the torso region. Accordingly, the operator utilizes the generated CT data and/or images to determine the desired axial coordinates in which the PET scan is to be conducted.

Accordingly, at step 120, for each target PET slice, the CT data is searched to determine whether the CT data includes any imaging data within the same series, the same examination, and including the same coordinates, i.e. the same patient orientation, as the coordinates that will be utilized to conduct the PET scan. More specifically, the CT data is analyzed to determine the slice locations of the CT data, and to determine if any of the CT slice data falls within the target PET slice. For example, the CT data is analyzed to determine if any CT slices are within the axial location of the PET slice that is to be generated. If a portion of the CT imaging data is selected, then the axial location of the selected CT images is determined at Step 122. More specifically, the start and end of each respective CT slice within the target PET slice is determined. After the axial location of the selected CT images has been determined in Step 122, the selected images are then analyzed in Step 124 to determine if any of the CT images overlap the desired PET scan region and/or whether there are multiple CT images within the desired PET scan region.

Figure 5A:
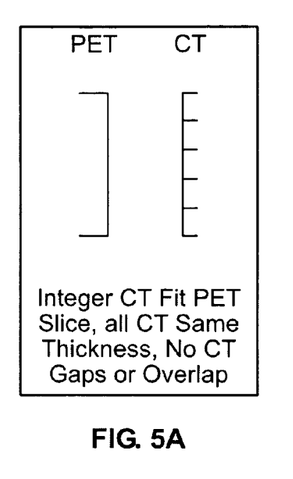
FIG. 5 is a pictorial view of a portion of the method shown in FIG. 3.
Figure 5B:
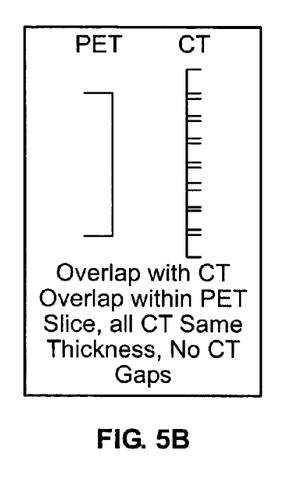
Figure 5C:
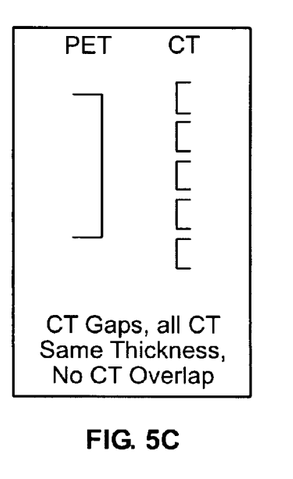
Figure 5D:
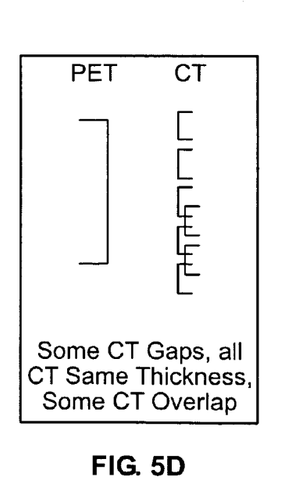
Figure 5E:
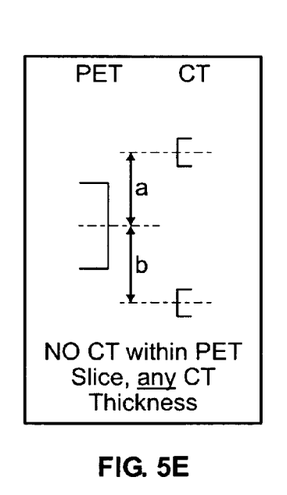
Figure 5F:
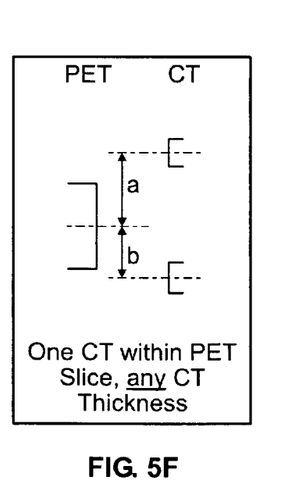

Referring to FIGS. 5a through 5f, the CT image data is analyzed to determine if any of the CT data is within the desired PET scan region. For example, FIG. 5a illustrates a plurality of non-overlapping adjacent CT images within the PET scan region, FIG. 5b illustrates a plurality of overlapping CT images within the PET scan region, FIG. 5c illustrates a plurality of non-overlapping CT images within the PET scan region wherein each image or slice is separated by a distance, FIG. 5d illustrates a plurality of overlapping and non-overlapping CT images within the PET scan region, FIG. 5e illustrates that no CT images or slices lie within the PET scan region, and FIG. 5f illustrates a case wherein at least a portion of one CT image lies within the PET scan region and a second CT slice lies outside the PET scan region.

Accordingly, at step 124 if it is determined that the PET scan region includes a plurality of overlapping CT images (shown in FIG. 5b), there are multiple CT images at the same location (shown in FIG. 5d) and/or there is at least one CT image that lies outside the PET scan region (FIGS. 5e and 5f), the selected CT images are utilized in Step 126. Alternatively, if a plurality of non-overlapping images are determined in Step 124 (shown in FIGS. 5a and 5c) the non-overlapping images are sent to a weighting algorithm 130 for further processing.

For example, at step 126, CT image data is analyzed to determine if any of the CT image data was taken within the same diameter of the field of view (dFOV), e.g. FIGS. 5a, 5b, 5c, 5d, and 5f. If at step 126 there is CT imaging data within the same DFOV, the selected CT image data with the larger dFOV is sent to the weighting algorithm at Step 130. Alternatively, if there is no selected CT imaging data within the selected dFOV, e.g. FIG. 5e, the CT imaging data is sent to step 128 where the image data is averaged together and then sent to the weighting algorithm at Step 130.

In the exemplary embodiment, selecting 102 CT imaging data to be utilized to generate CTAC data facilitates utilizing all the appropriate medical image quality CT data to generate PET attenuation correction factors while still allowing an operator to utilize specific CT techniques to generate the desired CT data image quality in different parts of the body.

The selected image data is then weighted 108 utilizing a weighting algorithm 130 that is configured to utilize the selected CT image data and combine the selected CT image data into a set of attenuation correction factors, also referred to an attenuation correction map, that are then utilized 110 to attenuation correct a PET image. During operation, weighting algorithm 130 is parameterized utilizing two factors that are used to control the quality of the CTAC data. The first factor is the maximum allowed extrapolation, applied at the axial ends of the calculation, and the second factor is the maximum gap in the CT image data. More specifically, during operation, if at least a portion of two CT slice lies within the axial boundaries of the PET slice, i.e. shown in FIGS. 5a, 5b, 5c, 5d, and 5f, weighting algorithm 130 is configured or programmed to receive four inputs that are determined based on the CT image data:

begin_pet: the axial location (mm) of the start of the PET slice;

end_pet: the axial location of the end of the PET slice;

begin_ct: axial location of the start of the CT slice; and end_ct: axial location of the end of the CT slice.

Utilizing the four inputs, weighting algorithm 130 calculates the weighting factor in accordance with:

$$B=\max([\text{begin\_pet}, \text{begin\_ct}])$$

$$E=\min([\text{end\_pet}, \text{end\_ct}])$$

Weighting factor=$E-B$ where max[a,b] returns the larger of a and b and min[a,b] returns the smaller of the two values.

When adding a CT slice to the integrated sum for a PET slice, it is multiplied by its weight and an integral of weighting factors is stored. After all CT slices are added to the sum slice, the sum slice is divided by the integral of weighting factors for all slices contributing to the PET slice. Optionally, if no CT slice lies within the axial boundaries of the PET slice (all weights are zero, Figure 5e), then the following weighting calculation is performed:

dist_lower=abs(pet slice center−lower CT slice center) {'b' in FIG. 5e} dist_upper=abs(pet slice center−upper CT slice center) {'a' in FIG. 5e} weight_CT_lower=dist_upper/(dist_lower+dist_upper)

weight_CT_upper=1.0−weight_CT_lower where abs defines taking absolute value and all slice centers are axial location, in mm. The weights are then applied to the lower and upper CT slices by multiplication. In use, the weight is larger for the CT slice with its center closer to the PET slice center. The weights are then used to calculate the weighted average of attenuation from the two CT images for the PET slice.

The method and apparatus described herein facilitate generating an attenuation correction map that can be utilized to remove the effects of attenuation and scatter from a PET image. Specifically, a plurality of attenuation correction factors (CTAC) are generated during a CT scan that is also useful to generate a diagnostic quality image for the CT purposes. For example, the CT scans for diagnostic purposes performed on the same patient may be acquired at different locations, using different slice thicknesses, during a helical, axial, and/or cine/gated scan technique, using different kV with/without contrast, with and/or without tilt.

During operation, PET scan data is acquired and processed as a sequence of axial frames along the length of the patient. Some instances of CT data that may be used for CTAC include, but are not limited to, one-to-one, i.e. one CT image covers one and only one PET slice, thin CT slices, i.e. more than one CT image will contribute to the PET slice CTAC, thick CT slices at short interval, i.e. multiple CT images are averaged together for PET slice CTAC, combined CT techniques, i.e. thin CT slices at some axial locations and thick CT slices at others, and CT image slices that are separated by gaps, i.e. the images are interpolated to generate PET slice CTAC using nearby CT images.

Accordingly, the method described herein facilitates allowing an operator to generate clinically useful CT images, in a realistic clinical scenario, to generate CT data at a spacing and technique that produces the most appropriate CT image set for a particular diagnostic scenario and also produces CT-based attenuation correction factors for associated PET data without having to perform a second CT scan to match the PET parameters.

As a result, the weighting scheme and data selection routines described herein enable a PET-CT system operator to generate correction data required for the PET portion of the scanner from the most clinically-relevant CT data available from the CT portion of the scanner. More CT imaging techniques are enabled to be used for both purposes, as well as removing a current restriction that requires a patient to be scanned by CT for CTAC in a manner that may not be the most clinically relevant from the CT diagnostic viewpoint.

The present invention is directed toward multi-modal imaging systems capable of scanning using different modalities, such as, for example, but not limited to, Positron Emission Tomography (PET) and Computed Tomography (CT). The difference between multi-mode and multi-modality is that multi-mode systems are utilized to perform scans in different modes (e.g., a fluoro mode and a tomosynthesis mode), while a multi-modal system (multi-modality system) is utilized to perform scans in different modalities (e.g., CT and PET). It is contemplated that the benefits of the invention accrue to all multi-modality imaging systems, such as, for example, but not limited to, a CT/PET imaging system.

While the invention has been described in terms of various specific embodiments, those skilled in the art will recognize that the invention can be practiced with modification within the spirit and scope of the claims.

The invention claimed is:

1. A method for correcting Positron Emission Tomography (PET) data comprising:
   generating a plurality of computed tomography (CT) image data;
   selecting a portion of the CT image data;
   processing the selected CT data to generate a plurality of computed tomography attenuation correction (CTAC) factors;
   weighting the CTAC factors to generate a PET attenuation correction map wherein the weights are determined based on an axial location and a slice thickness of the CT data and an axial location and a slice thickness of the PET data; and
   utilizing the generated attenuation correction map to generate an attenuation corrected PET image.

2. The method in accordance with claim 1 wherein selecting a portion of the CT data further comprises:
   determining slice locations of the CT data;
   analyzing the determined slices to determine if any of the CT slice data are within the axial location of the PET scan region; and
   selecting at least two CT slices that are positioned within the axial location of the PET scan region.

3. The method in accordance with claim 1 wherein selecting a portion of the CT data comprises:
   identifying slice locations of the CT data within axial locations of the PET data; and
   determining the start and end of each selected CT slice within the PET scan region.

4. The method in accordance with claim 1 wherein selecting a portion of the CT data comprises:
   identifying slice locations of the CT data; and
   determining if any of the identified CT slices lie within the PET scan region.

5. The method in accordance with claim 1 wherein selecting a portion of the CT data comprises:
   identifying slice locations of the CT data that lie within the PET scan region; and
   determining the quantity of CT slices within the PET scan region.

6. The method in accordance with claim 1, wherein the weighting factor is determined by at least two adjacent CT images that lie within the axial location of the PET scan, the CT images are at least one of overlapping CT images and non-overlapping CT images where all the CT images have the same slice thickness.

7. The method in accordance with claim 1, wherein the weighting factor is determined by at least two CT images that lie within the axial location of the PET scan, the CT images are separated by a distance and all the CT images have the same slice thickness.

8. The method in accordance with claim 1, wherein the weighting factor is determined by averaging at least two CT images together, the CT images do not lie within the axial boundaries of the PET scan region.

9. The method in accordance with claim 8, wherein the weighting factor is determined by interpolating CT images, the CT images are at least one of a thin CT slice and a thick CT slice where each CT image is separated by a distance.

10. The method in accordance with claim 1, wherein the weighting factor is determined by combining CT images where a CT image is at least one of a thin CT slice and a thick CT slice.

11. An imaging system for imaging a patient, said system comprising:
   a CT unit having a patient bore therethrough;
   a PET unit having a patient bore therethrough;
   a control mechanism communicatively coupled to said CT and PET units to control movement of said CT and PET units; and
   a computer coupled to said CT and PET units; said computer programmed to:

(i) process a selected portion of CT data to generate a plurality of computed tomography attenuation correction (CTAC) factors;

(ii) weight the CTAC factors to generate a PET attenuation correction map, wherein the weights are determined based on an axial location and a slice thickness of the CT data and an axial location and a slice thickness of a PET scan region; and (iii) utilize the generated attenuation correction map to generate an attenuation corrected PET image.

12. The imaging system in accordance with claim 11 wherein said computer is further programmed to:

determine slice locations of the CT data;

analyze the determined slices to determine if any of the CT slice data are within the axial location of the PET scan region; and select at least two CT slices that are positioned within the axial location of the PET scan region.

13. The imaging system in accordance with claim 11 wherein said computer is further programmed to:

identify a plurality of slice locations of the CT data; and determine the start and end of each selected CT slice within the PET scan region.

14. The imaging system in accordance with claim 11 wherein said computer is further programmed to:

select slices of CT data; and determine the quantity of the selected CT slices that lie within the PET scan region.

15. The imaging system in accordance with claim 11 wherein said computer is further programmed to determine a weighting factor by:

identifying adjacent CT images within the PET scan region, where the CT images are at least one of an overlapping CT image and a non-overlapping CT image;

determining a slice thickness for the CT images as being at least one of a thin slice and a thick slice; and selecting the CT images having the same slice thickness.

16. A computer program embodied on a computer readable medium for correcting Positron Emission Tomography (PET) data, said program configured to:

process a selected portion of CT data to generate a plurality of computed tomography attenuation correction (CTAC) factors;

weight the CTAC factors to generate a PET attenuation correction map wherein the weights are determined based on an axial location and a slice thickness of the CT data and an axial location and a slice thickness of the PET data; and utilize the attenuation correction map to generate an attenuation corrected PET image.

17. The computer program in accordance with claim 16 further programmed to:

determine slice locations of the CT data;

analyze the CT slice data to determine if any of the CT slices are within the axial location of the PET scan region; and select at least two CT slices that are positioned within the axial location of the PET scan region.

18. The computer program in accordance with claim 16 further programmed to:

select CT slices in the CT data that are positioned within the PET scan region; identify the start and end of each selected CT slice within the PET scan region; and determine the quantity of the selected CT slices that lie within the PET scan region.

19. The computer program in accordance with claim 16 further programmed to determine a weighting factor by:

identifying adjacent CT images within the PET scan region, where the CT images are at least one of an overlapping CT image and a non-overlapping CT image;

determining a slice thickness for the CT images as being at least one of a thin slice and a thick slice; and selecting the CT images having the same slice thickness.

* * * * *